US009386908B2

(12) United States Patent
Finkman et al.

(10) Patent No.: US 9,386,908 B2
(45) Date of Patent: Jul. 12, 2016

(54) NAVIGATION USING A PRE-ACQUIRED IMAGE

(71) Applicant: Gyrus ACMI, Inc., Southborough, MA (US)

(72) Inventors: Shai Finkman, Haifa (IL); Tali Portnoy, Binyamina (IL)

(73) Assignee: GYRUS ACMI, INC. (D.B.A. OLYMPUS SURGICAL TECHNOLOGIES AMERICA), Southborough, MA (US)

( * ) Notice: Subject to any disclaimer, the term of this patent is extended or adjusted under 35 U.S.C. 154(b) by 544 days.

(21) Appl. No.: 13/752,407

(22) Filed: Jan. 29, 2013

(65) Prior Publication Data

US 2014/0210971 A1   Jul. 31, 2014

(51) Int. Cl.
*A61B 1/04* (2006.01)
*A61B 1/00* (2006.01)
*G06T 7/00* (2006.01)

(52) U.S. Cl.
CPC ......... *A61B 1/00059* (2013.01); *A61B 1/00009* (2013.01); *A61B 1/043* (2013.01); *G06T 7/003* (2013.01); *G06T 7/0016* (2013.01); *G06T 2207/10068* (2013.01)

(58) Field of Classification Search
CPC .... A61B 1/00009; A61B 1/43; G06T 7/0014; G06T 7/0016; G06T 7/003; G06T 7/0044; G06T 2207/10068; G06K 9/3233
See application file for complete search history.

(56) References Cited

U.S. PATENT DOCUMENTS

| 5,550,582 | A | 8/1996 | Takasugi et al. |
| 5,675,378 | A | 10/1997 | Takasugi et al. |
| 7,356,172 | B2 * | 4/2008 | Fan et al. ...................... 382/128 |
| 7,450,151 | B2 | 11/2008 | Kaneko |
| 7,935,048 | B2 | 5/2011 | Yaron et al. |
| 2004/0019253 | A1 | 1/2004 | Tsujita et al. |
| 2005/0074151 | A1* | 4/2005 | Chen et al. .................... 382/128 |
| 2005/0182319 | A1 | 8/2005 | Glossop |
| 2006/0009452 | A1* | 1/2006 | Atamas .............. A61K 31/5377 514/232.8 |
| 2006/0210132 | A1* | 9/2006 | Christiansen et al. ........ 382/128 |

(Continued)

FOREIGN PATENT DOCUMENTS

| JP | 2004213398 A | 7/2004 |
| WO | 2005102175 A2 | 11/2005 |
| WO | 2012002312 A1 | 1/2012 |

OTHER PUBLICATIONS

International Application # PCT/US14/12414 Search Report dated Apr. 3, 2014.

*Primary Examiner* — John P Leubecker
(74) *Attorney, Agent, or Firm* — D.Kligler I.P. Services Ltd.

(57) ABSTRACT

A method for imaging, including capturing an initial image of a surface under investigation using a first endoscope, and delineating within the initial image a target region of interest surrounded by an initial image peripheral region, the target region of interest having a location defined with respect to the initial image peripheral region. The method includes capturing a subsequent image of the surface under investigation using a second endoscope and identifying in the subsequent image, by comparison with characteristics of the initial image peripheral region, a subsequent image peripheral region corresponding to the initial image peripheral region. The further includes computing the location of the target region of interest in the subsequent image in response to the identified subsequent image peripheral region.

7 Claims, 12 Drawing Sheets

(56) References Cited

U.S. PATENT DOCUMENTS

| | | |
|---|---|---|
| 2007/0135803 A1 | 6/2007 | Belson |
| 2007/0195165 A1* | 8/2007 | Hirakawa .................. 348/75 |
| 2008/0262297 A1* | 10/2008 | Gilboa et al. ............... 600/109 |
| 2009/0074270 A1 | 3/2009 | Tanaka et al. |
| 2010/0164950 A1* | 7/2010 | Zhao et al. ................. 345/419 |
| 2010/0249507 A1 | 9/2010 | Priseo et al. |
| 2010/0260392 A1* | 10/2010 | Wiemker et al. ............ 382/128 |
| 2011/0060185 A1 | 3/2011 | Ikuma et al. |
| 2011/0245642 A1 | 10/2011 | Minetoma |
| 2012/0088981 A1* | 4/2012 | Liu et al. ................... 600/300 |
| 2012/0130171 A1* | 5/2012 | Barak et al. ................ 600/117 |
| 2013/0070069 A1* | 3/2013 | Hyde et al. ................. 348/65 |
| 2013/0287259 A1* | 10/2013 | Ishii ........................... 382/103 |
| 2013/0338437 A1* | 12/2013 | Abuzaina .................... 600/109 |
| 2014/0079320 A1* | 3/2014 | Hamming et al. ........... 382/190 |
| 2014/0112529 A1* | 4/2014 | Park et al. ................... 382/103 |

* cited by examiner

NAVIGATION USING A PRE-ACQUIRED IMAGE

FIELD OF THE INVENTION

The present invention relates generally to imaging, and specifically to endoscope imaging systems that may be used on a repeated basis.

BACKGROUND OF THE INVENTION

There are many cases where an endoscope is used to image a given entity, typically a body cavity, multiple times, such as in tracking the effect of a medical procedure. A system which improves the ability to compare the multiple images would be advantageous.

SUMMARY OF THE INVENTION

An embodiment of the present invention provides a method for imaging, including:

capturing an initial image of a surface under investigation using a first endoscope;

delineating within the initial image a target region of interest surrounded by an initial image peripheral region, the target region of interest having a location defined with respect to the initial image peripheral region;

capturing a subsequent image of the surface under investigation using a second endoscope;

identifying in the subsequent image, by comparison with characteristics of the initial image peripheral region, a subsequent image peripheral region corresponding to the initial image peripheral region; and computing the location of the target region of interest in the subsequent image in response to the identified subsequent image peripheral region.

Typically the method includes characterizing the initial image peripheral region to generate the initial image peripheral region characteristics.

In a disclosed embodiment the first and second endoscopes are a common endoscope.

In a further disclosed embodiment the method includes generating target characteristics of the target region of interest surrounded by the initial image peripheral region, and computing the location of the target region of interest in the subsequent image includes verifying a commonality of the target characteristics with characteristics of a subsequent image target region surrounded by the subsequent image peripheral region. In an embodiment the method further includes determining the characteristics of the subsequent image target region without performing a medical procedure on the target region of interest and after capturing the initial image.

In an alternative embodiment the method includes generating target characteristics of the target region of interest surrounded by the initial image peripheral region, and computing the location of the target region of interest in the subsequent image includes verifying a difference between the target characteristics and characteristics of a subsequent image target region surrounded by the subsequent image peripheral region. Typically, the method also includes determining the characteristics of the subsequent image target region after capturing the initial image and after performing a medical procedure on the target region of interest.

There is further provided, according to an embodiment of the present invention imaging apparatus, including:

a first endoscope configured to capture an initial image of a surface under investigation using a first endoscope;

a second endoscope configured to capture a subsequent image of the surface under investigation; and a processor configured to:

delineate within the initial image a target region of interest surrounded by an initial image peripheral region, the target region of interest having a location defined with respect to the initial image peripheral region, identify in the subsequent image, by comparison with characteristics of the initial image peripheral region, a subsequent image peripheral region corresponding to the initial image peripheral region, and compute the location of the target region of interest in the subsequent image in response to the identified subsequent image peripheral region.

There is further provided, according to an embodiment of the present invention a method for imaging, including:

pointing to a target region of interest in a first image;

storing image data of a peripheral region surrounding the target region of interest;

identifying in a second image, by comparison with characteristics of the stored image data of the peripheral region, a region corresponding to the peripheral region of the first image; and marking a location of the target region of interest in the second image in response to the identified region in the second image.

There is further provided, according to an embodiment of the present invention a method for navigating an endoscope, including:

capturing a first image of a surface under investigation using a first endoscope;

pointing to a target region of interest in the first image;

storing image data of a peripheral region surrounding the target region;

capturing a second image of the surface under investigation using a second endoscope;

identifying in the second image, by comparison with characteristics of the stored image data of the peripheral region, a region corresponding to the peripheral region;

marking an indication of a location of the target region of interest in the second image in response to the identified region in the second image; and navigating the second endoscope toward the indication.

The present invention will be more fully understood from the following detailed description of the embodiments thereof, taken together with the drawings in which:

DETAILED DESCRIPTION OF EMBODIMENTS

Overview

An embodiment of the present invention provides a method for locating a common region in images of a surface that have been captured at differing times. The method may be used in an endoscopic examination of an internal surface of a body cavity, such as the abdomen or bladder of a patient. Typically, the method is used to navigate an endoscope towards the common region in an initial examination, and then in a subsequent examination, of the body cavity surface.

A first endoscope is inserted into the body cavity, and an initial image of the surface is captured. Within the initial image a target region of interest is delineated, typically by marking an external bound of the target region with a cursor. Surrounding the target region of interest, and comprised in the initial captured image, is an initial image peripheral region. The two regions are related geometrically, so that the target region of interest can be considered to have a location defined by the initial image peripheral region.

A second endoscope is inserted into the body cavity, and is used to capture a subsequent image of the surface. Characteristics of the two images are compared, and the characteristics are used to identify a peripheral region of the subsequent image that corresponds to the initial image peripheral region. The location of the target region of interest in the subsequent image is computed using the identified peripheral region of the subsequent image.

A marker may be placed in the subsequent image, at the computed location, as an aid to navigating to, as well as identifying, the target region of interest.

In some embodiments the first and second endoscopes are the same endoscope.

Detailed Description

Figure 1:
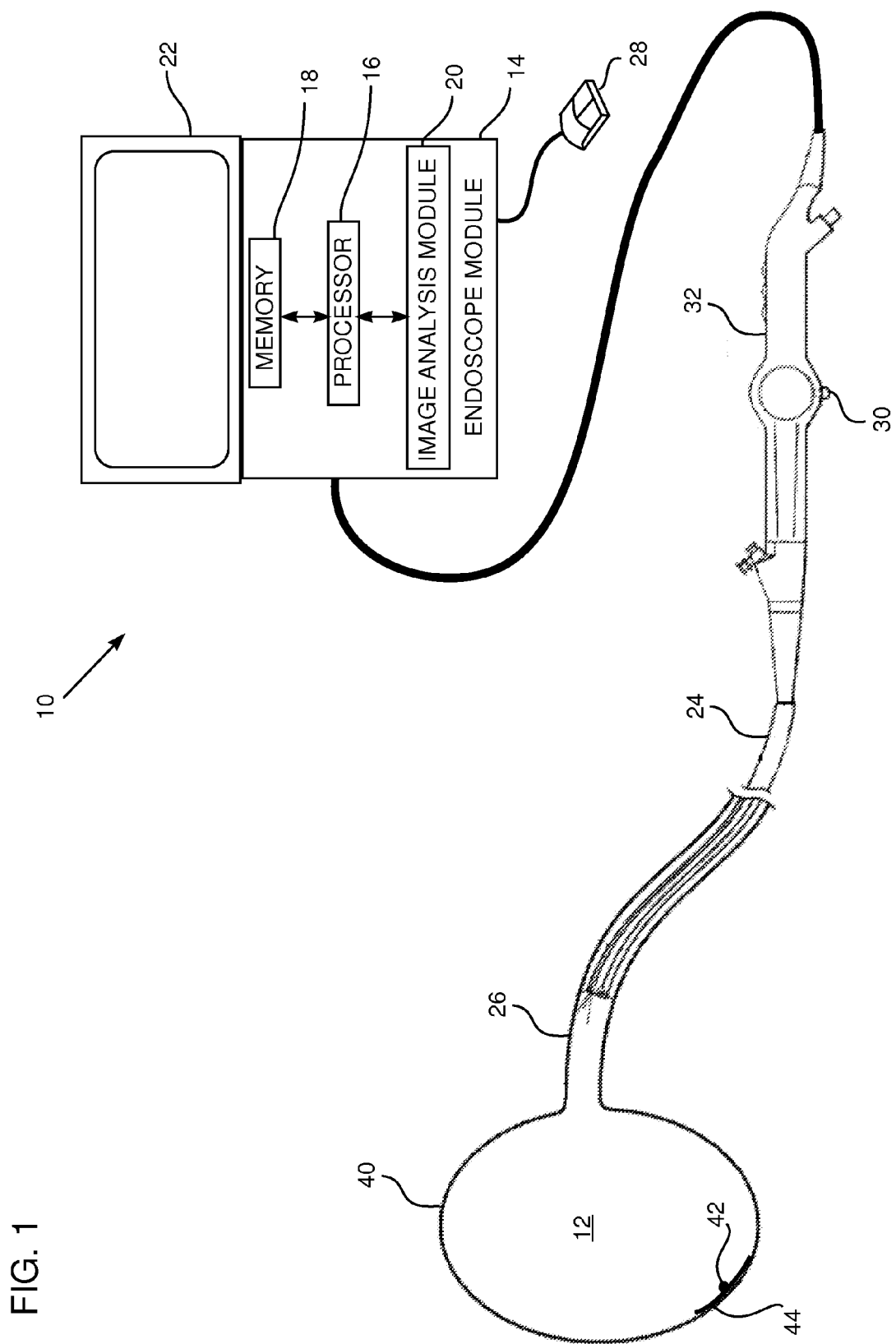
FIG. 1 is a schematic illustration of an endoscope navigation system, according to an embodiment of the present invention.

Reference is now made to FIG. 1, which is a schematic illustration of an endoscope navigation system 10, according to an embodiment of the present invention. System 10 may be used in an invasive medical procedure, typically a minimally invasive procedure, on a body cavity 12 of a human patient in order to image entities in the body cavity. By way of example, in the present description, except where otherwise indicated, the body cavity is assumed to be the bladder of a patient, and body cavity 12 is also referred to herein as bladder 12. However, it will be understood that system 10 may be used on substantially any human body cavity, such as the gastrointestinal organs, the bronchium, the chest, or on a non-human cavity.

System 10 is controlled by an endoscope module 14, comprising a processor 16 communicating with a memory 18. Endoscope module 14 also comprises an image analysis module 20, whose functions are described below, and which may be implemented in software, hardware, or a combination of software and hardware. Endoscope module 14 typically also comprises other modules, such as cavity illumination modules, which may be used by the processor in operating the endoscope module; for simplicity these modules are not shown in the figure.

The processor uses software, typically stored in memory 18, to control system 10. Results of the actions performed by processor 16 may be presented on a screen 22 to an operator, usually a medical physician, of system 10. The screen typically displays images of body cavity 12 undergoing the procedure, and/or a graphic user interface, to the operator. The software for operating system 10 may be downloaded to processor 16 in electronic form, over a network, for example, or it may, alternatively or additionally, be provided and/or stored on non-transitory tangible media, such as magnetic, optical, or electronic memory.

To perform a procedure, an endoscope 24 may be passed to bladder 12 through a urethral tube 26. Endoscope module 14 provides illumination for the endoscope and displays an image acquired by the endoscope on screen 22. The operator typically uses the endoscope to view the interior of bladder 12. Interactive module controls 28 are coupled to module 14, and enable the operator of system 10 to control functions of the module. Module controls 28 may comprise any convenient system known in the art, such as a pointing device, a touch screen, and/or a keypad. By way of example, controls 28 are assumed to comprise a mouse, as is illustrated in the figure.

Endoscope 24 is operated using endoscope controls 30, which by way of example are assumed to be located in a handle 32 of the endoscope. Exemplary functions of controls 30 are described below.

A typical procedure performed by system 10 comprises the operator performing an initial inspection of walls 40 of body cavity 12 using the endoscope. During the inspection, a suspicious entity 42 may be identified in a region 44 of the body cavity, as explained in more detail below.

Reference is now made to FIGS. 2, 3, 4A, 4B, 5A, 5B, 5C, and 6.

Figure 2:
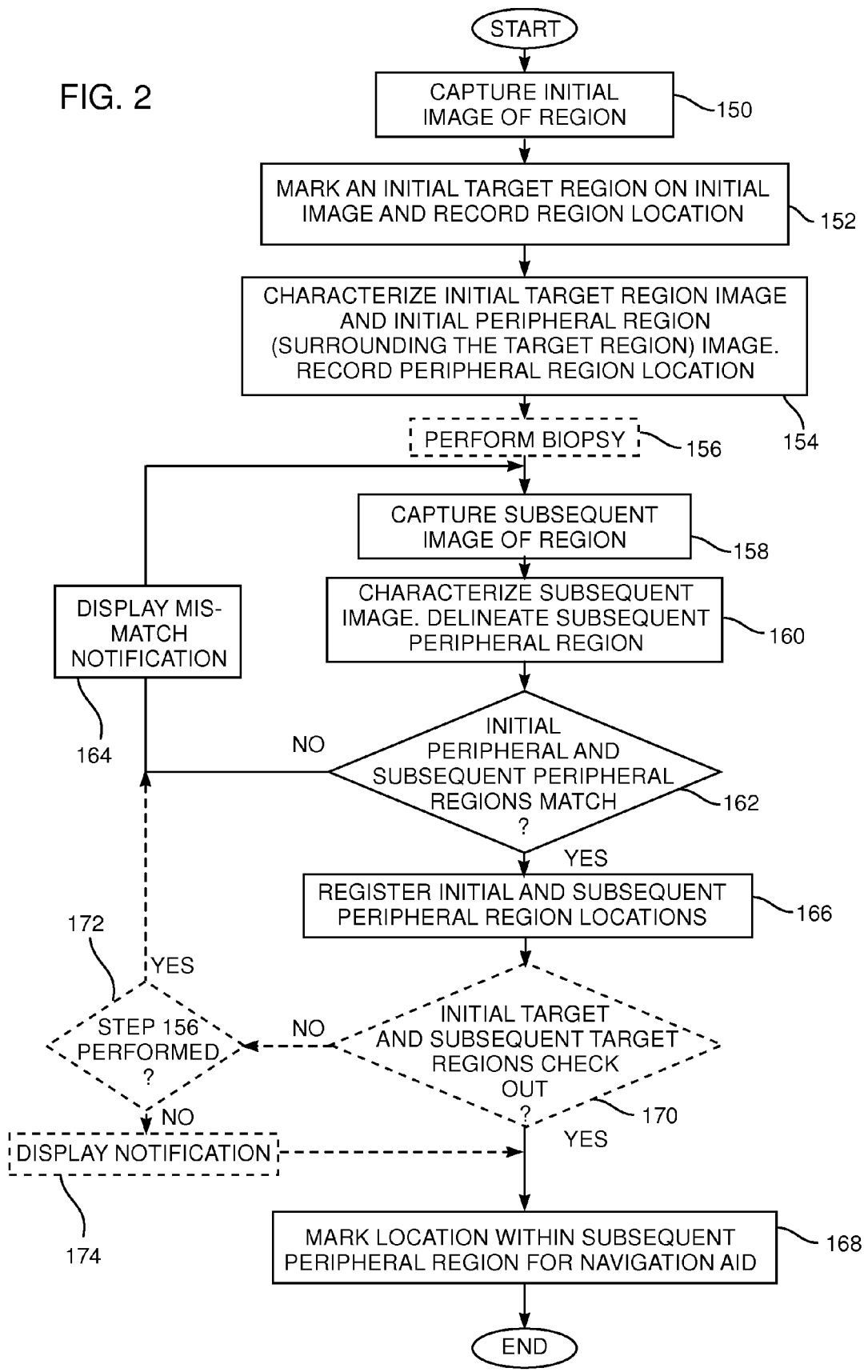
FIG. 2 is a flowchart of a process performed using the system, according to an embodiment of the present invention.
Figure 3:
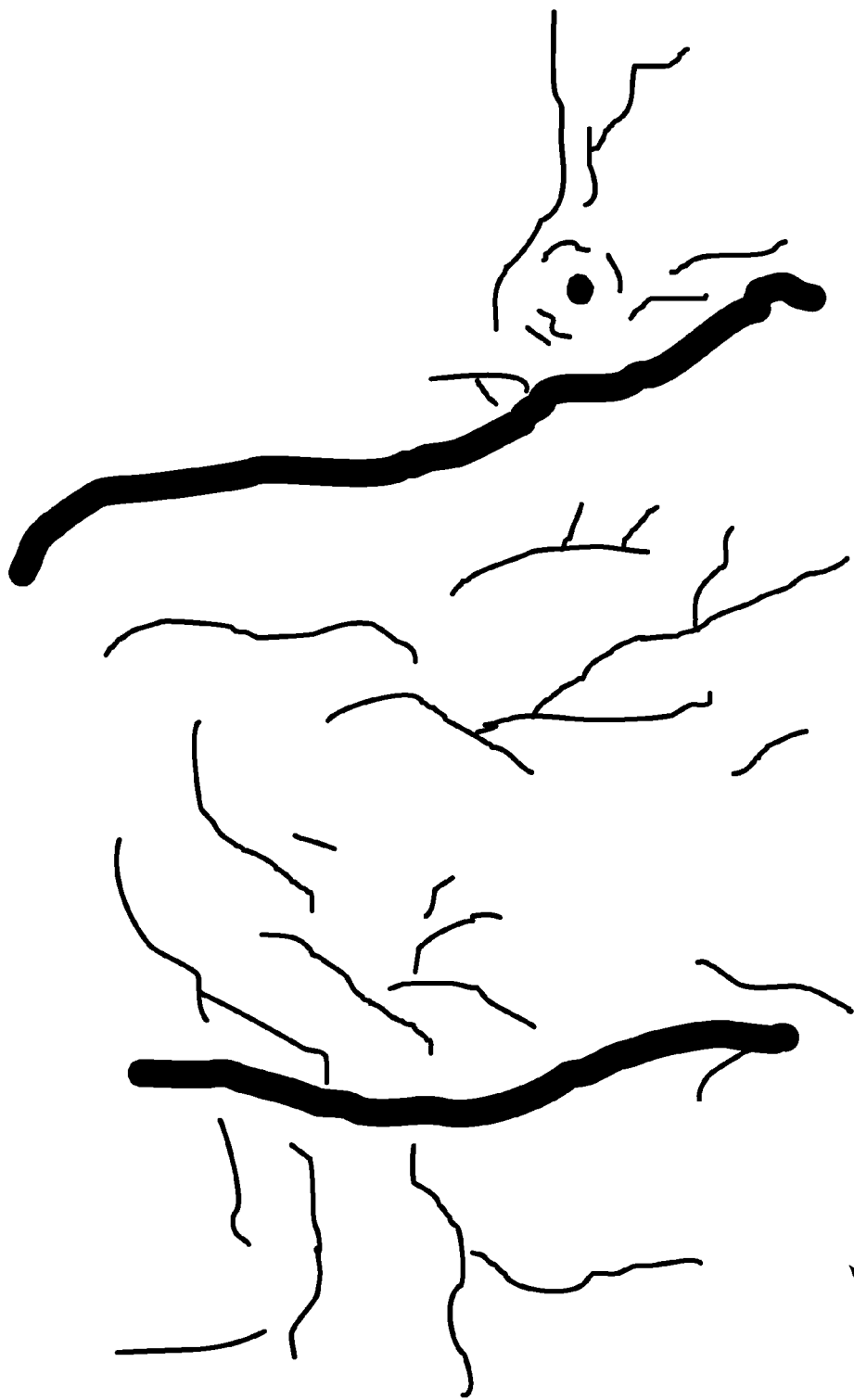
FIG. 3 is a schematic illustration of an initial image captured by the system, according to an embodiment of the present invention.
Figure 4A:
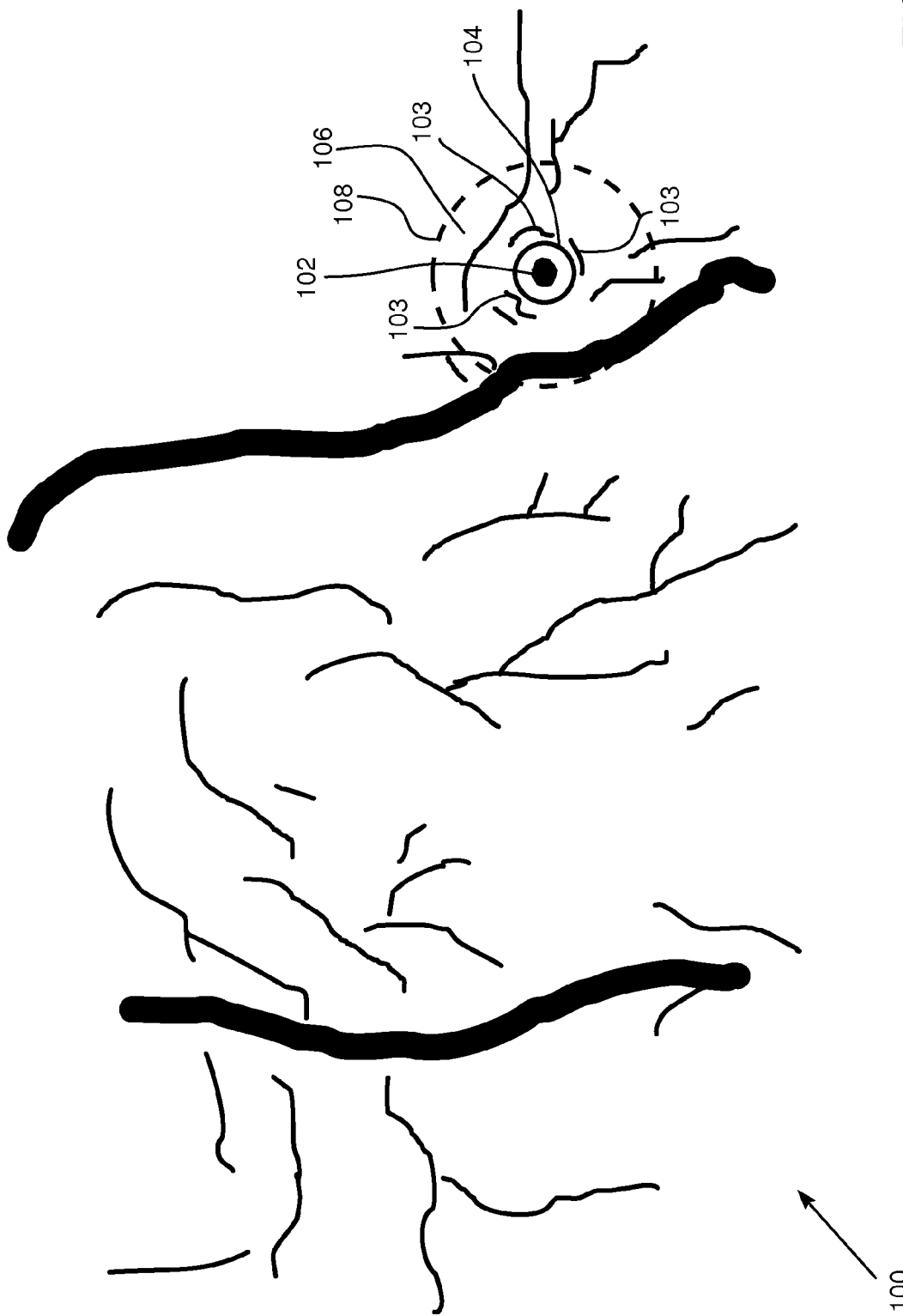
FIG. 4A is a schematic illustration of the initial image marked with a target region of interest and FIG. 4B is an enlarged section of FIG. 4A, according to an embodiment of the present invention.
Figure 4B:
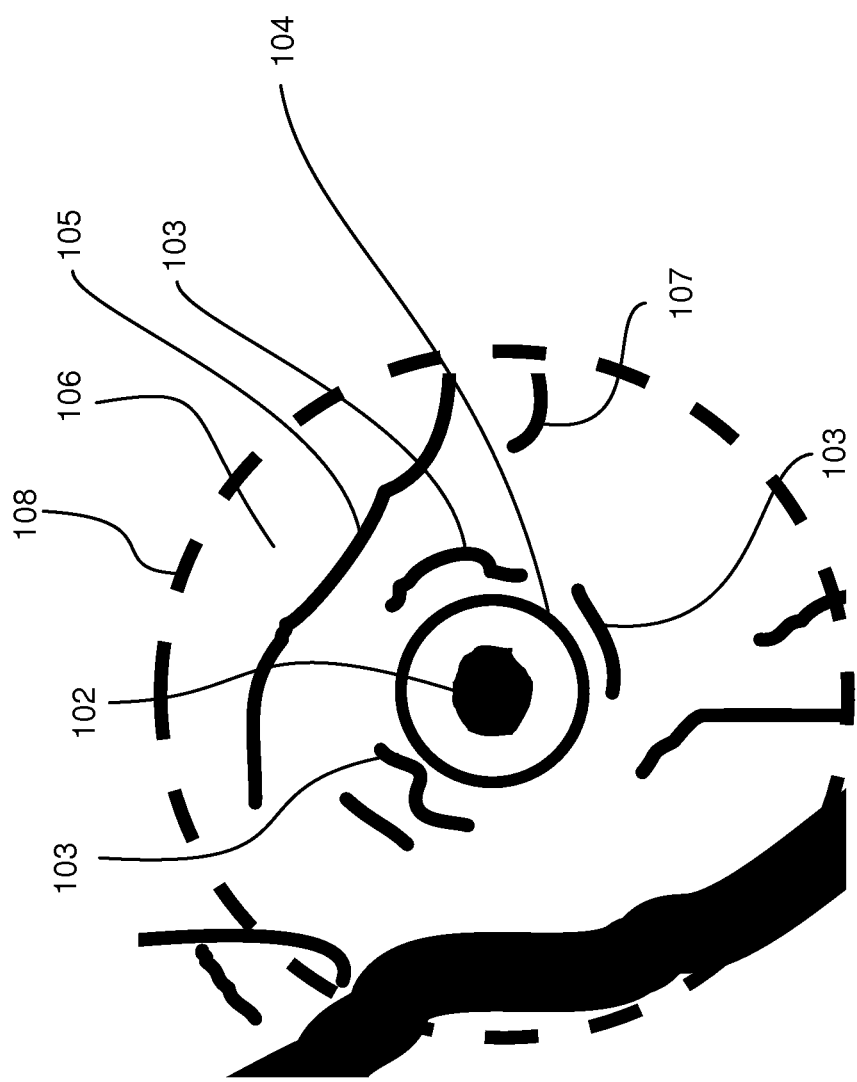
Figure 5A:
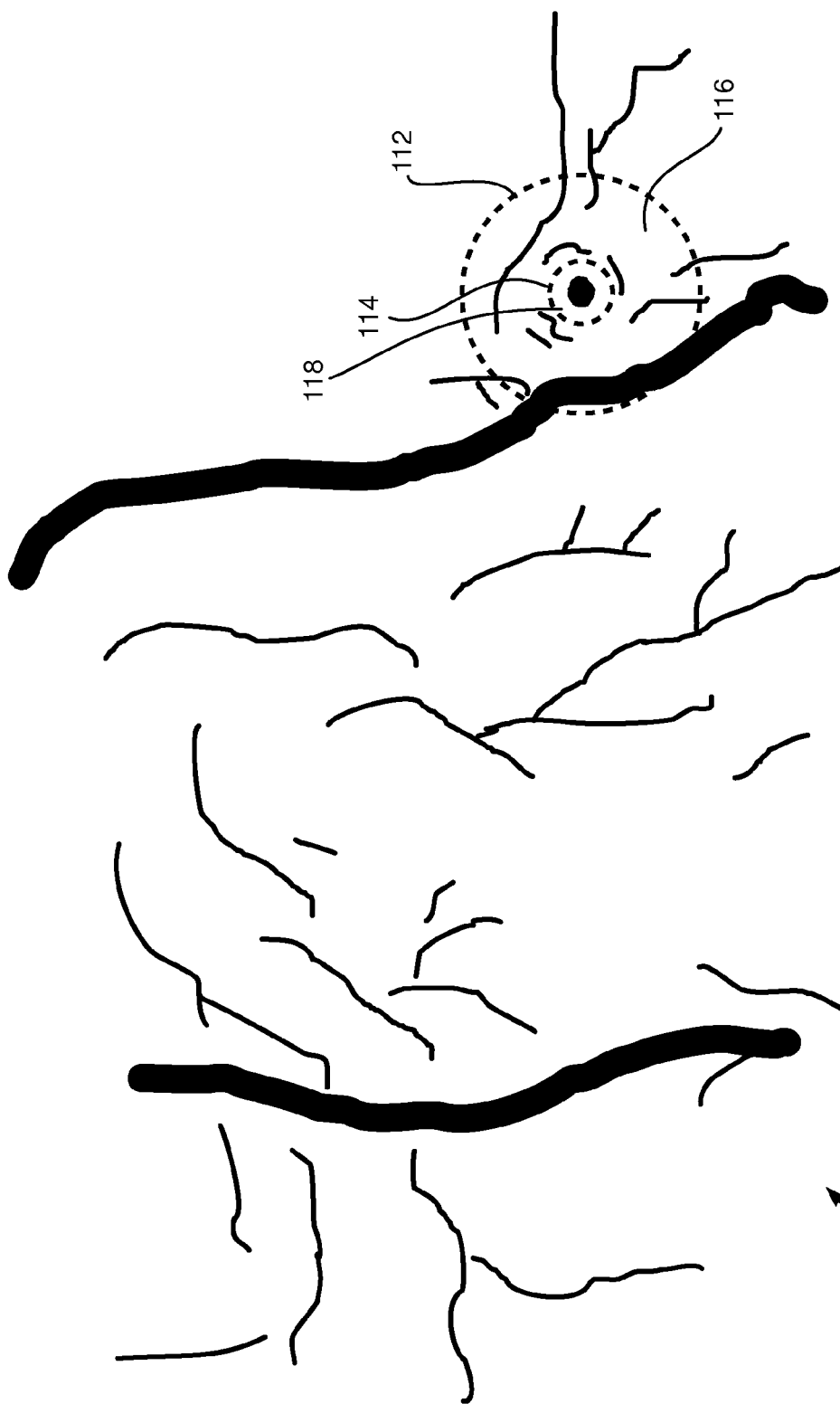
FIGS. 5A, 5B, and 5C are schematic illustrations of different subsequent images captured by the system, according to embodiments of the present invention.
Figure 5B:
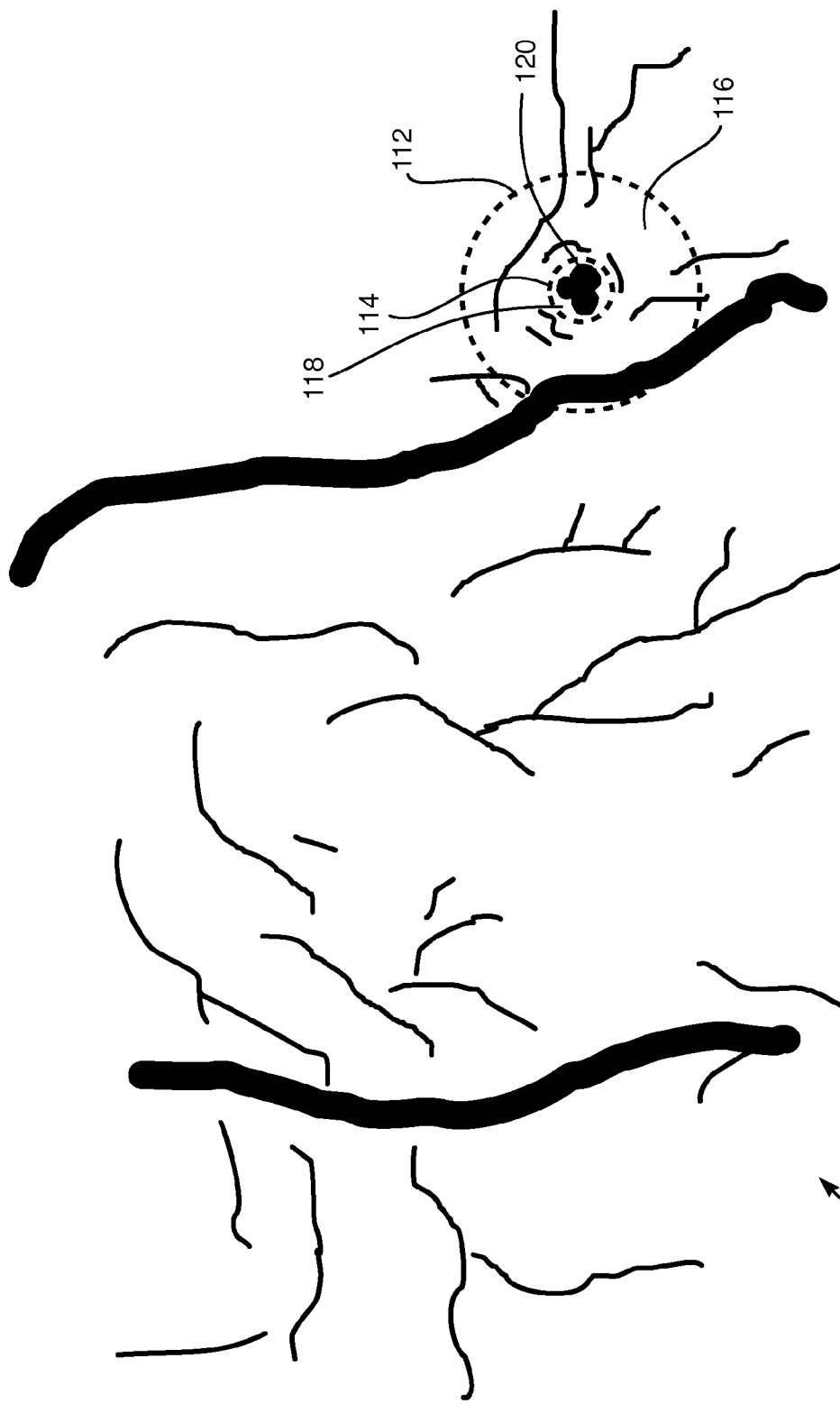
Figure 5C:
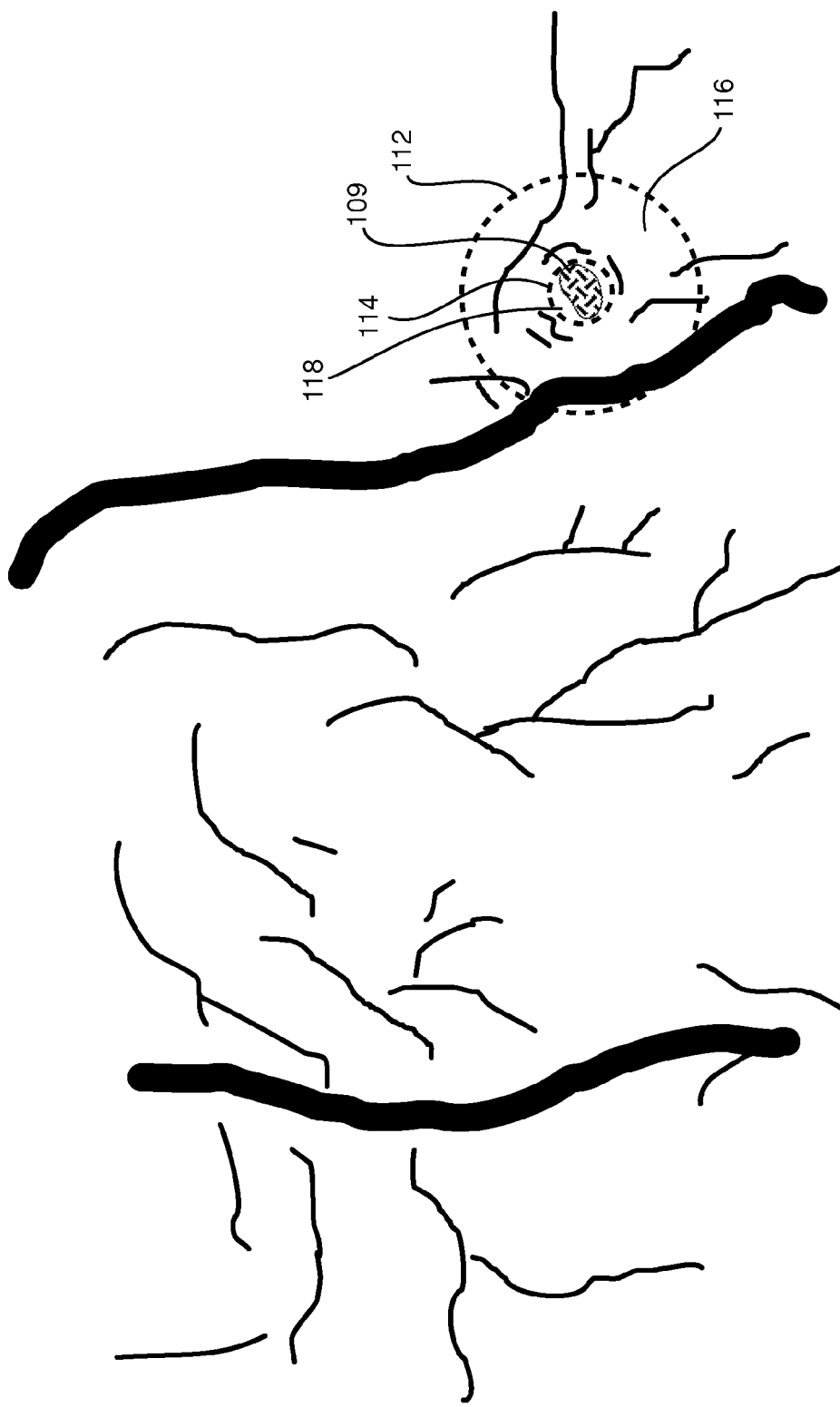
Figure 6:
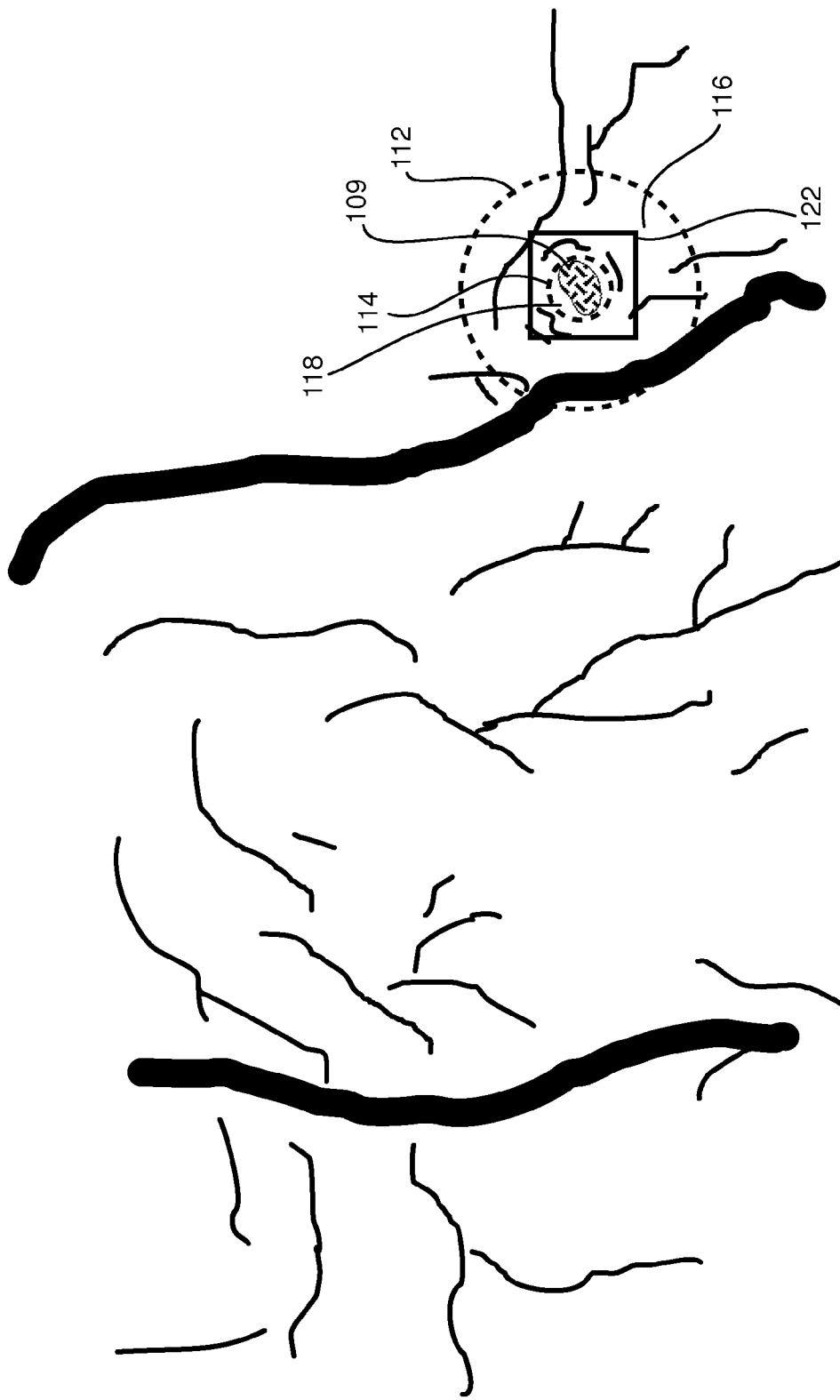
FIG. 6 is a schematic illustration of a marker applied to one of the subsequent images, according to an embodiment of the present invention.

FIG. 2 is a flowchart of a process performed using system 10, according to an embodiment of the present invention; FIG. 3 is a schematic illustration of an initial image of bladder 12 captured by the system, according to an embodiment of the present invention; FIG. 4A is a schematic illustration of the initial image marked with a target region of interest, and FIG. 4B is an enlarged section of FIG. 4A, according to an embodiment of the present invention; FIGS. 5A, 5B, and 5C are schematic illustrations of different subsequent images of the bladder captured by the system, according to embodiments of the present invention; and FIG. 6 is a schematic illustration of a marker applied to one of the subsequent images, according to an embodiment of the present invention.

The process illustrated by the flowchart is implemented by processor 16, using image analysis module 20. Except where otherwise stated, the process is assumed to be performed using endoscope 24.

In an initial step 150 of the process, the operator of system 10 inserts endoscope 24 into bladder 12. The endoscope is operated to point to and capture an initial image of a region under investigation, such as region 44, and to display the captured image to the operator on screen 22. Using the displayed image, the system operator manipulates endoscope 24 so that the captured image is an initial image 100, shown schematically in FIG. 3, of the region under investigation.

In a marking step 152, the system operator delineates an initial target region of interest 102 within image 100, as shown schematically in FIGS. 4A and 4B. The delineation is typically performed by the operator moving a cursor 104 within image 100, using controls 28, until the cursor surrounds the target region, the cursor acting as an outer bound of the target region. After delineation processor 16 records a location, within the image captured in step 150, of the initial target region of interest. In the example illustrated here, initial target region of interest 102 is surrounded by, for example, three biological elements of interest 103. While cursor 104 is depicted as circular in FIGS. 4A and 4B, the cursor may be any convenient shape.

In a first characterization step 154, processor 16 characterizes the initial target region, within the bounds of cursor 104. The processor also characterizes an initial peripheral region 106 surrounding the initial target region 102, and the processor then stores the characterizations of both regions. The initial peripheral region has as its inner bound cursor 104, and typically has an outer bound 108 which may comprise any convenient bounding figure within image 100. In one embodiment, outer bound 108 is assumed to be a circle centered on the center of target region 102, having an area a pre-set multiple, such as ten, of the area of target region 102. However, the operator of system 10 may define outer bound 108 as any convenient bounding figure with the confines of image 100. Once processor 16 has set the bounds of the initial peripheral region, the processor records a location, within the image captured in step 150, of the peripheral region. The recorded location is typically the center of the peripheral region.

It will be understood that the initial target and peripheral regions are related geometrically, as are their locations. Thus, the initial target region location may be considered to be defined with respect to the peripheral region, and the peripheral region location may be considered to be defined with respect to the initial target region.

In the case of both the target region and the peripheral region, the characterization is of such a type as to enable the processor to use elements of the image identified in the characterization for matching a section of a future image to either the target region or the peripheral region. Typically the elements identified by the characterization comprise significant biological elements in the regions, such as capillaries, larger blood vessels, epithelium pits, suspected tumors, and areas of the mucosal surface being imaged. Identified elements are typically enumerated. In addition, identified elements are typically characterized by color, as well as by geometrical factors such as the size and shape of the element. In some embodiments areas to be characterized are visually enhanced prior to the characterization, such as by fluorescent imaging. A suitable visual enhancing technique that may be applied is the Narrow Band Imaging technology available from Olympus Corporation, Tokyo, Japan.

Thus, in the example illustrated by FIGS. 3, 4A and 4B, processor 16, using module 20, typically enumerates and morphologically qualifies by size, shape, and/or color one or more elements of target region 102. For peripheral region 106, in addition to enumerating and morphologically qualifying by size, shape, and/or color elements 103 the processor may also enumerate and qualify, by way of example, two blood vessels 105 and 107 (FIG. 4B) as elements in characterizing the peripheral region. Processor 16 typically also enumerates and morphologically qualifies other elements of target region 102 and peripheral region 106. The qualification by shape typically comprises quantifying concavities, convexities, inflexions, and/or other shape-defining features of an enumerated element.

In an optional procedure performing step 156, the operator executes a medical procedure on target region 102. The procedure may comprise any procedure that changes the characteristics of the target region, as measured in step 154. The procedure is typically a biopsy, although any other procedure that changes the target region characteristics, such as the application of a pharmaceutical or chemical agent to the target region, may be performed in step 156. In addition, in step 156 the operator uses controls 28 to inform processor that a medical procedure on target region 102 has been performed. The processor uses this information in step 170, described below.

In a subsequent imaging step 158, a second image of the region under investigation is captured. As is described in more detail below, the second image may be divided into a number of categories. Different categories of the second image are referred to collectively as second image 110, and exemplary different image categories are illustrated in FIGS. 5A, 5B and 5C. As is illustrated in FIGS. 5A, 5B and 5C, different second images 110 are differentiated by appending a letter to the numeral 110, as second images 110A, 110B, and 110C.

Endoscope 24 may be used to capture the second image; alternatively, another endoscope may be used to capture the second image. The endoscope used to capture the second image may be inserted into bladder 12. While second image 110 is captured at a time after the capture of initial image 100 of the region under investigation, there is substantially no limit on the time period between the capture of the two images. For example, in a follow-up inspection of the region under investigation, second image 110 may be acquired three months after the initial image. However, embodiments of the present invention comprise time periods that may be smaller or greater than three months.

Depending whether step 156 has been performed, as well as on whether there have been changes in the target region of interest during the time period between the acquisition of the initial and second images, there may or may not have been changes in the characteristics of the target region of interest. Image 110A (FIG. 5A) illustrates a case where there is substantially no change between the two images. Image 110B (FIG. 5B) illustrates a case where there has been a change between the two images, even though step 156 has not been performed, i.e., there has been no intervening procedure performed on the region under investigation. Image 110C (FIG. 5C) illustrates a case where there has been a change between the two images when step 156 has been performed after acquisition of the initial image, so that an intervening procedure has been performed.

In a second characterization step 160, processor 16 characterizes image 110. The characterization is generally as for first characterization step 154, and provides identifying elements within the image similar to those described above for the first characterization step. Using the identifying elements, the processor delineates an outer bound 112 and an inner bound 114 of a subsequent peripheral region 116 comprising elements that correspond to the elements of the initial peripheral region (determined in first characterization step 154). In delineating outer bound 112 and inner bound 114, the processor only relates to, and attempts to match characteristics of, identifying elements of the initial peripheral region. In other words, in defining subsequent peripheral region 116 the processor does not consider identifying elements of the initial target region.

FIGS. 5A, 5B, and 5C illustrate, for subsequent peripheral region 116, an exemplary outer bound 112 and an exemplary inner bound 114 for each of the three images 110A, 110B, and 110C.

In a comparison 162 the processor checks that elements of initial peripheral region 106 (found in step 154) have a sufficiently good match to the elements of subsequent peripheral region 116. Typically, there are some changes over time between the elements in the initial peripheral region and those of the subsequent peripheral region. To allow for these changes, in deciding if a given element such as a blood vessel, is matched in the two peripheral regions, the processor may apply a first pre-set variation factor, typically of the order of 90%, in deciding if parameters of the given element correspond. In addition, the processor may use a second pre-set factor, typically of the order of 90%, in deciding if the number of elements in the two regions match.

If comparison 162 is not valid, in a return step 164 processor 16 typically may show a warning to the operator, on screen 22, that the system has been unable to match the initial and subsequent peripheral regions, and the flowchart returns to step 158. In the warning the operator may be prompted to re-orientate the endoscope to capture a new subsequent image in step 158.

If comparison 162 is valid, in a registration step 166 the processor records a location of the subsequent peripheral region within the image captured in step 158. The processor then registers the location of the subsequent peripheral region with the location of the initial peripheral region, the latter location on the captured image having been recorded in step 154. The flowchart may then proceed directly to a final step 168, described below. In some embodiments, the flowchart optionally first proceeds to a comparison 170 (indicated as being optional in the flowchart by the use of broken lines).

In optional comparison 170, the processor compares elements of initial target region 102 with elements of a subsequent target region 118, i.e., elements within inner bound 114. The processor performs the comparison by quantifying the measurement (the enumeration and morphological qualification) on the initial target region made in step 154, and quantifying a similar measurement of the subsequent target region. The processor then calculates the fraction of the two quantities. If there is little or no change between the initial and subsequent target regions, the fraction is close to 1. Conversely, if there is a relatively large change, the fraction is close to zero. An expected value of the fraction depends, inter alia, on whether the procedure of step 156 has been performed or not, as explained below. (If the procedure of step 156 has been performed, the processor is notified, as described above.)

If step 156 has been performed, typically comprising taking a biopsy of region 102 (FIGS. 4A and 4B), the processor records this and sets the expected value of the fraction to be low. An embodiment of the present invention sets the expected value of the fraction, for cases where step 156 has been performed, to be typically of the order of 10% or even lower in evaluating comparison 170. The comparison is assumed to be valid if the measured fraction for the two regions is less than or equal to the expected fraction, since a low fraction of matches confirms that subsequent target region 118 is different in morphology from initial target region 102. Such a different morphology, and corresponding low fraction for the comparison of the two target regions, is expected if a biopsy or other procedure has been performed at the location of the target regions between the times of acquiring the initial target region image and the subsequent target region image. If comparison 170 is valid, the flowchart continues at final step 168.

If comparison 170 is not valid, the flowchart continues to a comparison 172, where the processor checks if step 156 has been performed. If step 156 has been performed, the flowchart returns, via return step 164 (described above) to step 158.

Image 110C (FIG. 5C) illustrates a case where step 156 has been performed. As shown, the element of target region 102 is not present, and in its place there is scar tissue 109. It will be understood that if only the element of target region 102 and scar tissue 109 are considered in evaluating the second comparison, the measured fraction equals zero and for the embodiment described above the comparison is valid since the fraction is less than 10%.

If, in comparison 170, step 156 has not been performed, there is typically a commonality of characteristics in the initial and subsequent target regions, and the value of the expected fraction comparing the two regions is typically high. In one embodiment the processor sets the expected fraction used in comparison 170 (when step 156 has not been performed) to be approximately 50%, and the comparison is assumed to be valid if the measured fraction is greater than the expected fraction.

Image 110A (FIG. 5A) illustrates a case where elements of subsequent target region 118 are substantially the same as elements of initial target region 102. Such a case typically occurs where there has been no morphological change in the target region of interest in the time between acquisition of the two images. In this case the measured fraction comparing the two regions is approximately 1, which is greater than 50%, so that comparison 170 is valid and the flowchart continues to final step 168.

Image 110B (FIG. 5B) illustrates a case where an element 120 of subsequent target region 118 has changed compared to elements of initial target region 102. In the example illustrated, there has been morphological change in the target region of interest in the time between acquisition of the two images. In this case the measured fraction comparing the two regions is assumed to be less than 50%, so that comparison 170 is invalid and the flowchart continues to comparison 172.

In this case comparison 172 is invalid, since step 156 has not been performed, so that the flowchart continues, after a notification step 174, to final step 168. In notification step 174 the processor displays a notification to the operator, on screen 22, that there may have been a change, such as a morphological change, in the target region of interest.

In final step 168, the processor uses subsequent peripheral region 116 to identify a region corresponding to initial target region 102 (delineated in the initial image by cursor 104) in subsequent image 110. The identification is possible since the processor is aware of the relation between the initial target and peripheral regions, and since locations of the initial peripheral and subsequent peripheral regions have been registered (in step 166). The processor marks the corresponding region in subsequent image 110 with a marker 122, the marker indicating to the operator the site of the initial target region in the subsequent image. FIG. 6 illustrates marker 122 as applied to image 110C. (While marker 122 has been drawn as a square, it may be any convenient shape.) Typically, the system 10 operator may use marker 122 to confirm the location of initial target region 102, and/or to navigate more closely to the target region.

Figure 7:
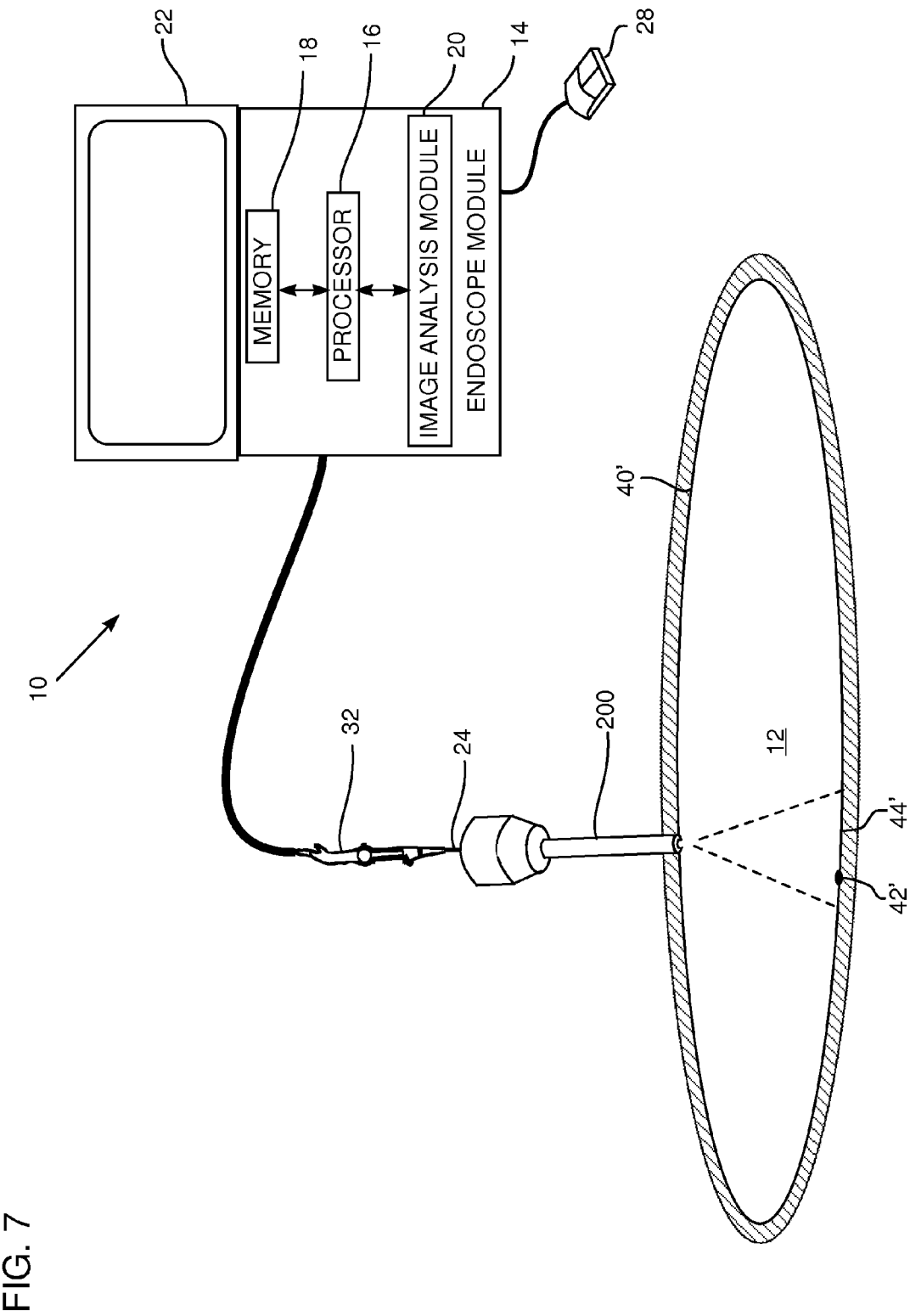
FIG. 7 is a schematic illustration of the endoscope navigation system, according to an alternative embodiment of the present invention.
Figure 8:
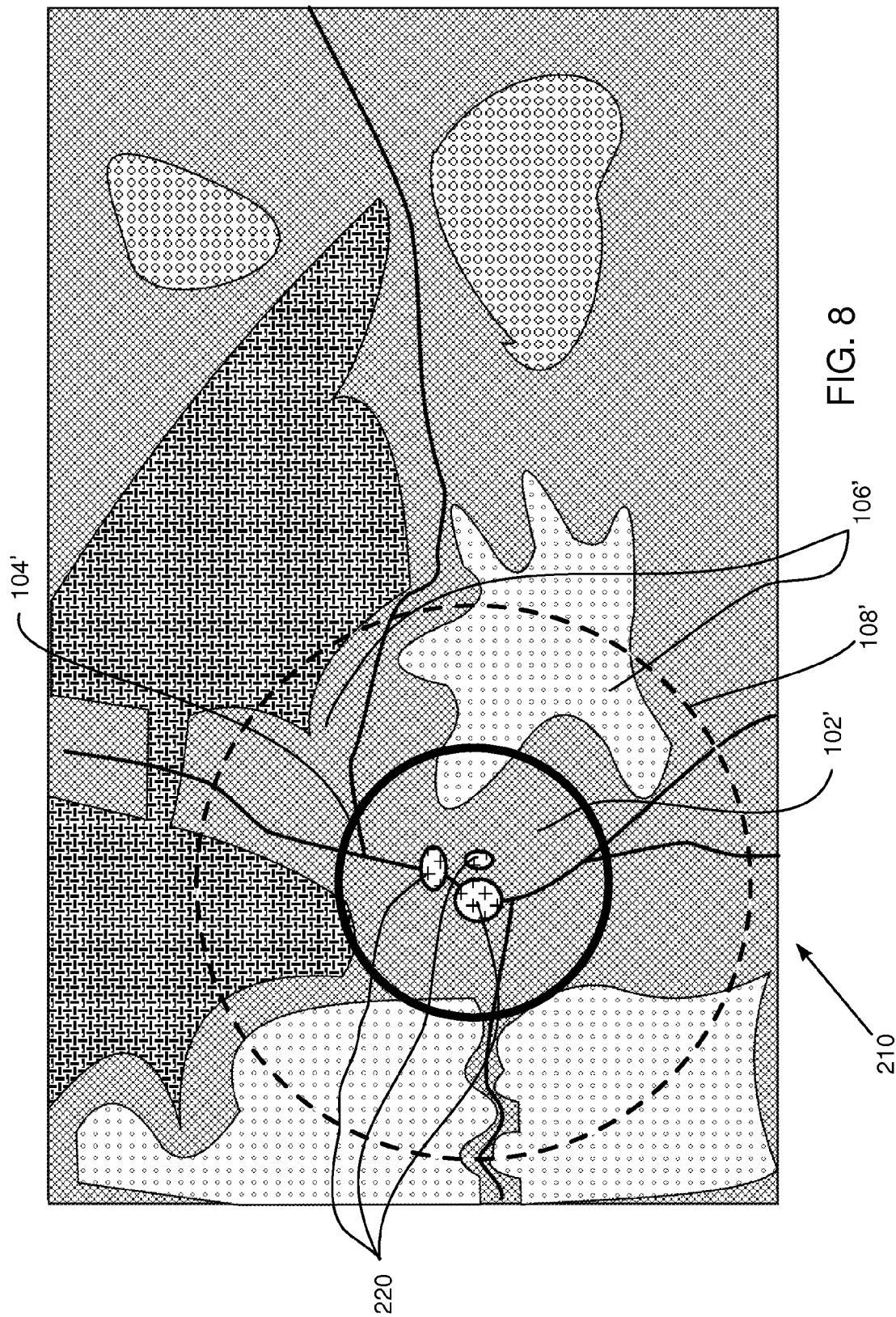
FIG. 8 is a schematic illustration of an alternative initial image captured by the system, according to an embodiment of the present invention.
Figure 9:
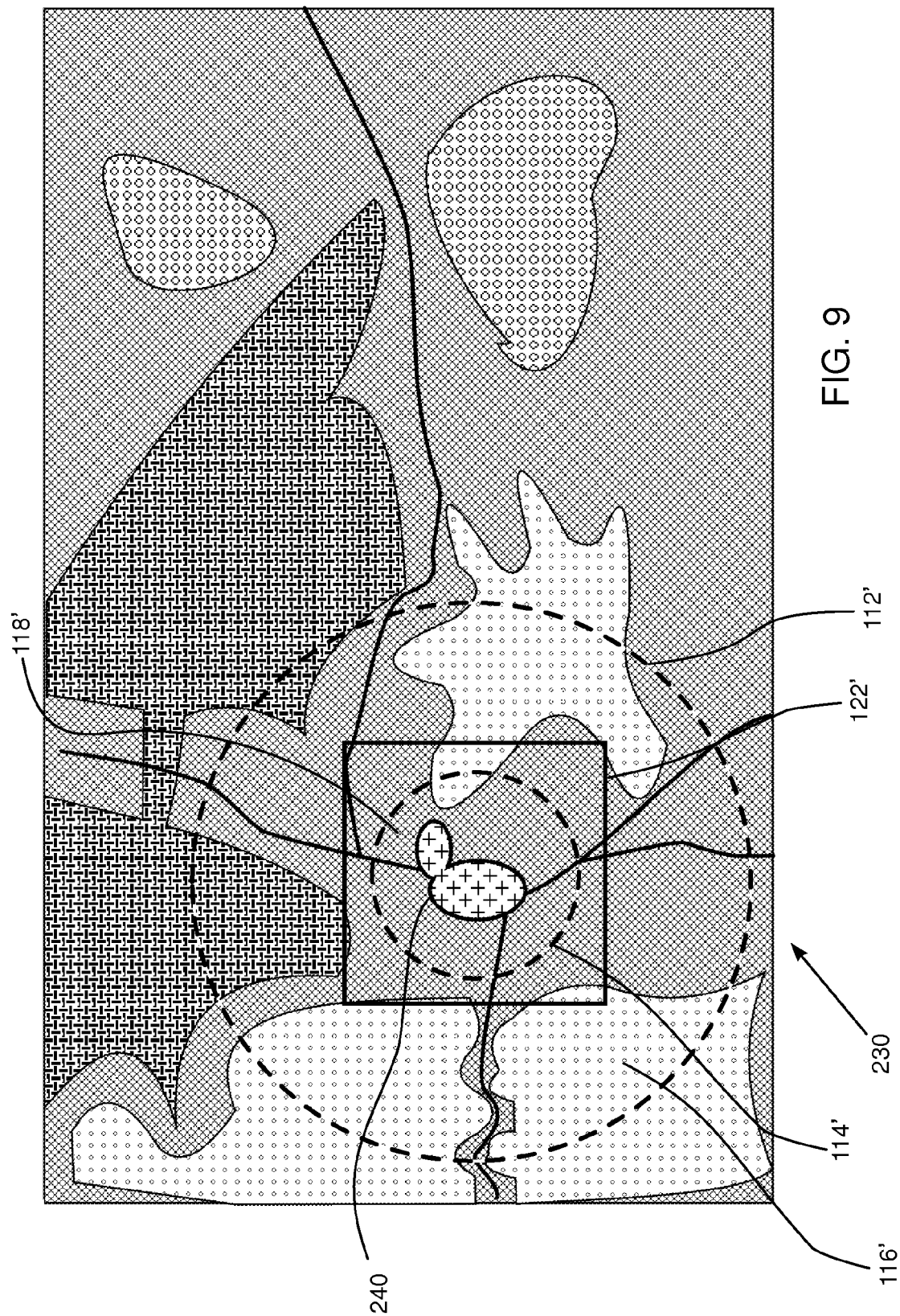
FIG. 9 is a schematic illustration of an alternative subsequent image captured by the system, according to an embodiment of the present invention.

FIG. 7 is a schematic illustration of endoscope navigation system 10, according to an alternative embodiment of the present invention. In the following description the body cavity investigated by the system is assumed to be the abdomen of the patient, and hereinbelow the abdomen is referred to as abdomen 12. Reference is also made to FIGS. 8, and 9. FIG. 8 is a schematic illustration of an initial image of abdomen 12 captured by system 10, and FIG. 9 is a schematic illustration of a subsequent image of the abdomen captured by the system, according to embodiments of the present invention.

Apart from the differences described below, the operation of system 10 in investigating abdomen 12 is generally similar to that of the system as described above with reference to investigation of the bladder, and elements indicated by the same reference numerals in both descriptions are generally similar in construction and in operation. For clarity, in the following description of the investigation of the abdomen, some of the similar elements are differentiated by having an apostrophe ' appended to the reference numeral.

The flowchart of FIG. 2 applies to the operation of system 10 in investigating abdomen 12.

Referring to steps 150, 152, and 154 of the flowchart, and to FIG. 7, endoscope 24 is inserted into abdomen 12 via a trocar 200, which is used to penetrate walls 40' of the abdomen. The endoscope is manipulated by handle 32 to inspect a suspicious entity 42' of a region 44' of the walls.

FIG. 8 illustrates a schematic initial image 210 of abdomen 12 that is captured by the endoscope. As explained above with reference to FIG. 4A and step 154, using controls 28 a cursor 104' is moved to surround an initial target region 102'. Processor 16 sets an outer bound 108', and uses cursor 104' and outer bound 108' as the bounds of an initial peripheral region 106'. As is also explained above, the processor characterizes the initial target and peripheral regions.

By way of example, initial target region 102' is assumed to include three biological elements of interest 220, and in its characterization of the initial target region 102' in step 154, as explained above, processor 16 uses this number.

In the investigation of abdomen 12 there is no biopsy or other procedure performed on initial target region 102', so that step 156 of the flowchart is not implemented, and the flowchart continues to steps 158, 160, and 162. FIG. 9 illustrates a subsequent image 230 captured in step 158. As explained above with respect to steps 160 and 162, the processor delineates an outer bound 112' and an inner bound 114' of a subsequent peripheral region 116', and compares the initial and subsequent peripheral regions. The comparison is assumed to be valid, so that the flowchart continues to step 166.

System 10 is assumed to apply optional comparison 170, so that the flowchart continues from step 166 to comparison 170, wherein initial target region 102' and a subsequent target region 118', within inner bound 114', are compared. In comparison 170, since step 156 has not been performed, the value of the expected fraction used in the comparison is set high, and by way of example is assumed to be 50%.

As illustrated in FIG. 9, the three elements 220 have coalesced to one element 240, and in comparison 170 the value of the measured fraction, comparing the morphology of the initial and subsequent target regions is less than the value of the expected fraction. The flowchart then proceeds to comparison 172, and since step 156 has not been performed, to notification step 174 and final step 168. In step 174 the processor may display a notification on screen 22 that there may have been a morphological change in the target region of interest. In step 168 the processor uses the location of peripheral region 116' (determined in step 166) to position a marker 122' in subsequent image 230, to indicate to the operator the site of the initial target region in the subsequent image.

It will be appreciated that the embodiments described above are cited by way of example, and that the present invention is not limited to what has been particularly shown and described hereinabove. Rather, the scope of the present invention includes both combinations and subcombinations of the various features described hereinabove, as well as variations and modifications thereof which would occur to persons skilled in the art upon reading the foregoing description and which are not disclosed in the prior art.

The invention claimed is:

1. A method for endoscopic evaluation, comprising:
capturing an initial image of a surface under investigation using a first endoscope;
delineating within the initial image a target region of interest containing first elements, surrounded by a peripheral region containing second elements, the target region of interest having a location defined with respect to the peripheral region;
performing a first characterization of the first elements in the initial image, thereby generating an initial target region measure;
recording information indicating that a medical procedure was executed after capturing the initial image;
after capturing the initial image, capturing a subsequent image of the surface under investigation using a second endoscope;
identifying the peripheral region in the subsequent image, by matching elements appearing in the subsequent image to the second elements in the initial image, irrespective of the first elements in the target region;
computing the location of the target region of interest in the subsequent image in response to the peripheral region identified in the subsequent image;
performing a second characterization of the target region in the computed location in the subsequent image, thereby generating a subsequent target region measure;
comparing the initial and subsequent target region measures by computing a fraction of the initial and subsequent target region measures;
setting a first predetermined threshold value if the information is recorded before acquiring the subsequent image; and
confirming that the procedure has been performed when the fraction of the initial and subsequent target region measures is less than the first predetermined threshold value.

2. The method according to claim 1, wherein the first and second endoscopes comprise a common endoscope.

3. The method according to claim 1, and comprising:
navigating the second endoscope toward the target region based on the identified peripheral region in the subsequent image.

4. The method according to claim 1, further comprising:
setting a second predetermined threshold value if the information is not recorded before acquiring the subsequent image; and
marking the target region in the computed location in the subsequent image as a region corresponding to the target region of the initial image.

5. An apparatus for endoscopic evaluation, comprising:
a first endoscope configured to capture an initial image of a surface under investigation using a first endoscope;
a second endoscope configured to capture a subsequent image of the surface under investigation after capturing the initial image; and a processor configured to:

delineate within the initial image the target region of interest containing first elements, surrounded by a peripheral region containing second elements, the target region of interest having a location defined with respect to the peripheral region, perform a first characterization of the first elements in the initial image, thereby generating an initial target region measure, record information indicating that a medical procedure was executed after capturing the initial image, identify the peripheral region in the subsequent image, by matching elements appearing in the subsequent image to the second elements in the initial image, irrespective of the first elements in the target region, compute the location of the target region of interest in the subsequent image in response to the peripheral region identified in the subsequent image, perform a second characterization of the target region in the computed location in the subsequent image, thereby generating a subsequent target region measure, compare the initial and subsequent target region measures by computing a fraction of the initial and subsequent target region measures, set a first predetermined threshold value if the information is recorded before acquiring the subsequent image, and confirm that the procedure has been performed when the fraction of the initial and subsequent target region measures is less than the first predetermined value.

6. The apparatus according to claim 5, wherein the first and second endoscopes comprise a common endoscope.

7. The apparatus according to claim 5, wherein the processor is configured to set a second predetermined threshold value if the information is not recorded before acquiring the subsequent image, and to mark the target region in the computed location in the subsequent image as a region corresponding to the target region of the initial image.

* * * * *